(12) United States Patent
Toyoda et al.

(10) Patent No.: US 6,251,612 B1
(45) Date of Patent: Jun. 26, 2001

(54) MONOCLONAL ANTIBODY FOR IMMUNOASSAY OF DETERGENTS AND THEIR DEGRADATION PRODUCTS AND ITS USE

(75) Inventors: Yukio Toyoda, Hyogo; Masanori Fujita, Osaka; Yasuhiro Goda, Hiroshima; Ken-ichiro Miyagawa; Shigeru Fujimoto, both of Osaka, all of (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 08/942,915

(22) Filed: Oct. 2, 1997

(30) Foreign Application Priority Data

Oct. 4, 1996 (JP) .................................................. 8-264202
Aug. 27, 1997 (JP) .................................................. 9-230819

(51) Int. Cl.$^7$ .................................................. G01N 33/53
(52) U.S. Cl. ..................... 435/7.1; 435/7.92; 530/388.1; 530/388.9; 530/389.8
(58) Field of Search .................... 530/388.1, 388.9, 530/389.8; 435/7.1, 7.92

(56) References Cited

FOREIGN PATENT DOCUMENTS

92/15014   9/1992   (WO) .
94/12536   6/1994   (WO) .

OTHER PUBLICATIONS

Wong et al., J. Lipid Res. 26 (5). 1985, 528–539.*

* cited by examiner

Primary Examiner—Laurie Scheiner
(74) Attorney, Agent, or Firm—Foley & Lardner (57) ABSTRACT

A hybridoma obtainable by fusing a spleen cell or lymphocyte of an animal immunized by a complex of a surfactant compound for synthetic detergent and protein with a myeloma cell, which produces a monoclonal antibody against the compound or its degradation product. A monoclonal antibody against a surfactant compound for synthetic detergent or its degradation product which is produced by the hybridoma, a kit for immunoassay of detergent, its degradation product or a mixture thereof containing as an essential constitutional component the monoclonal antibody, and an immunoassay method, in particular, ELISA of detergent, its degradation product or a mixture thereof in a specimen by reacting the specimen with the monoclonal antibody supported on a carrier and the detergent, its degradation product or the mixture thereof labeled with a labeling agent are also disclosed.

31 Claims, 4 Drawing Sheets

MONOCLONAL ANTIBODY FOR IMMUNOASSAY OF DETERGENTS AND THEIR DEGRADATION PRODUCTS AND ITS USE

FIELD OF THE INVENTION

The present invention relates to a monoclonal antibody for an immunoassay of detergents and their degradation products, and its use. More specifically, it relates to a hybridoma which produces the monoclonal antibody, the monoclonal antibody produced by the hybridoma, and a kit and a method for immunoassay of detergents, their degradation products or a mixture thereof.

BACKGROUND OF THE INVENTION

Among surfactants for synthetic detergents, a linear alkylbenzenesulfonate (hereinafter sometimes abbreviated to LAS), which is an anionic surfactant, has been sold and used since 1967 instead of a branched alkylbenzenesulfonate (ABS), which has poor biodegradability, according to the recommendation of the administrative. Since LAS is cheap and its toxicity is low, it is still using as a main component of household synthetic detergents. However, recently, water pollution by LAS and its degradation products have been a social problem because of the discharge of drainage from living into rivers, etc. Then, the tap water standard of anionic surfactants has been established (not more than 0.2 mg/liter). In addition, nonionic surfactants are used as about 40% of surfactant compounds for synthetic detergents and establishment of its tap water standard is being studied.

Under these circumstances, synthetic detergents and their degradation products in an environment are determined and analyzed and the results are utilized for environmental preservation. As methods for such determination and analysis, for example, high-performance liquid chromatography (HPLC) and gas chromatography (GC) are employed for quantitative determination of detergents and their degradation products in tap water, rivers, swamps, lakes or sewege etc. However, the problems of these methods are such that they require expensive apparatus or devices, pretreatment and the operation with great skill. As official methods for measuring anionic surfactants and nonionic surfactants, there are methylene blue absorption method and potassium zinc (II) tetrathiocyanate method, respectively. However, these methods require, for example, extraction with organic solvents which are harmful to human beings and complicated concentration steps and therefore, improvement of these methods is expected.

In view of these problems, regarding anionic and nonionic surfactants, it is desired to develop a method for determination thereof which can maintain present high sensitivity and can be readily and quickly operated with high specificity at a low cost.

As one means for solving these problems, an enzyme-linked immunosorbent assay (hereinafter sometimes abbreviated to ELISA) can be considered.

Assay systems and kits utilizing ELISA have been constructed for various other environmental pollutants. For example, WO 94/12536 discloses ELISA for detecting petroleum fuel in an environment and a kit for such ELISA. The kit comprises an enzyme and an antibody, and the measurement can be completed very quickly, usually, within several hours. And, the operation is very simple in comparison with conventional HPLC and GC, and, in most cases, no complicated pretreatment required in such conventional methods is needed. Further, a very specific determination can be carried out by using an antibody, in particular, a monoclonal antibody. HPLC and GC require very expensive apparatus and devices and their maintenance is also expensive, while ELISA has no such problem.

However, any immunoassay method which can be used for detection and determination of synthetic detergents including LAS, in particular, ELISA has not yet been established.

OBJECTS OF THE INVENTION

In order to establish an immunoassay method for detection and determination of synthetic detergents, one object of the present invention is to provide a hybridoma which can produce a monoclonal antibody useful for an immunoassay of synthetic detergents, their degradation products and a mixture thereof.

Another object of the present invention is to provide the monoclonal antibody produced by the hybridoma of the present invention.

Another object of the present invention is to provide a kit for an immunoassay of synthetic detergents, their degradation products and a mixture thereof.

Still another object of the present invention is to provide a method for immunoassay of synthetic detergents, their degradation products and a mixture thereof.

These objects as well as other objects and advantages of the present invention will become apparent to a person skilled in the art from the following description with reference to the accompanying drawings.

SUMMARY OF THE INVENTION

The present inventors have studied to establish a method for immunoassay of LAS, APE and their degradation products, in particular, a method for detection and determination thereof by ELISA, intensively. As a result, it has been found that anti-LAS or anti-APE monoclonal antibody-producing hybridoma can be obtained by using SPC, which is an analogue of LAS, or a half ester of nonylphenol ethoxylate and succinic anhydride (hereinafter, sometimes, abbreviated to NP7EC), which is an analogue of APE, combining it with a carrier protein to obtain a complex, immunizing a mouse with the complex and isolating the hybridoma from its spleen. In addition, it has also been found that LAS, APE and their degradation products can be determined with high sensitivity by using the above monoclonal antibody and labeled LAS, APE and their degradation products. Thus, the present invention has been completed.

That is, according to the present invention, there is provided a hybridoma obtainable by fusing a spleen cell or lymphocyte of an animal immunized by a complex of a surfactant compound for synthetic detergent and a protein together with a myeloma cell, which produces a monoclonal antibody against the compound or its degradation product.

The present invention also provides a monoclonal antibody against a surfactant compound for synthetic detergent or its degradation product which is produced by the hybridoma of the present invention.

Further, the present invention provides a kit for immunoassay of detergent, its degradation product or a mixture thereof comprising as an essential constitutional component the monoclonal antibody of the present invention.

Furthermore, the present invention provides a method for immunoassay, in particular, ELISA of detergent, its degradation product or a mixture thereof in a specimen which comprises reacting the specimen with the monoclonal antibody of the present invention held on a carrier and the detergent, its degradation product or the mixture thereof labeled with a labeling agent, and then measuring the activity of either the labeling agent held on the carrier or the free labeling agent.

The present invention is applicable to detergents containing surfactants for synthetic detergents, for example, anionic surfactants and nonionic surfactants and, according to the present invention, such detergents, their degradation products or a mixture thereof can be analyzed immunologically with high sensitivity and specificity.

DETAILED DESCRIPTION OF THE INVENTION

The hybridoma of the present invention can be obtained according to a per se known method by using a complex of a surfactant compound for synthetic detergent and a protein (carrier protein).

Examples of the surfactant compounds for synthetic detergents to be used include anionionic surfactant compounds such as alkylsulfuric acid, alkylbenzenesulfonic acid, alkylnaphthalenesulfonic acid, naphthalenesulfonate-formaldehyde condensate and their salts (e.g., alkali metal salts, etc.); and nonionic surfactant compounds such as polyoxyethylene alkylphenyl ether, polyoxyethylene alkyl ether, polyoxyether polystyrylphenyl ether, polyoxyethylene styrenated phenyl ether and their salts (e.g., phosphate, sulfate, etc.). Examples of the "alkyl" used herein includes that having 2 to 18 carbon atoms. The surfactant compound can be appropriately selected according to the detergent to be analyzed and its degradation products. However, from the viewpoint of environmental preservation, to select LAS, APE or its salt is particularly desired.

As the carrier protein, for example, there are bovine serum albumin (hereinafter abbreviated to BSA), ovalbumin (hereinafter abbreviated to OVA) bovine thyroglobulin (hereinafter abbreviated to BTG) and the like.

The formation of the complex of the surfactant compound for synthetic detergent or its analogous compound and the protein can be carried out by combining a compound of the formula (I):

A—R          (I)

[wherein R is COOH, NH$_2$ or SH; and A is a group which forms the surfactant compound for synthetic detergent or its analogous compound by removal of R] to the protein according to a per se known method.

The compound of the formula (I) can also be synthesized chemically by introducing or forming a carboxyl group, amino group or sulfhydryl group in a suitable starting material according to a per se known method.

For example, the compound of the formula (I) wherein R is COOH and A is a group which forms LAS can be produced by sulfonating a phenylalkylcarboxylic acid, for example, phenyl valeric acid [J. Chromato., 178, 259 (1979)].

The compound of the formula (I) wherein R is COOH and A is a group which forms a polyoxyethylene alkylphenyl ether can be produced by subjecting a polyoxyethylene alkylphenyl ether and succinic anhydride to dehydration-condensation (formation of half ester) [Cancer Biochem. Biophys., 7, 175 (1984)].

The compound of the formula (I) wherein R is NH$_2$ and A is a group which forms LAS can be produced by sulfonating a chloroalkylbenzene, for example, 2-chloroethylbenzene [J. Chromato., 178, 259 (1979)], followed by treatment with ammonia (Organic Functional Group Preparations, Vol. 1, p. 382).

The compound of the formula (I) wherein R is NH2 and A is a group which forms a polyoxyethylene alkylphenyl ether can be produced by chlorinating the hydroxyl group of the polyoxyethylene alkylphenyl ether with thionyl chloride [J. Am. Chem. Soc., 60, 2540 (1938)], followed by treatment with ammonia (Organic Functional Group Preparations, Vol. 1, p. 382].

The compound of the formula (I) wherein R is SH and A is a group which forms LAS can be produced by sulfonating a chloroalkylbenzene, for example, 2-chloroethylbenzene [J. Chromato., 178, 259 (1979)], followed by reaction with sodium hydrosulfide [J. Am. Che. Soc., 72, 1843 (1950)].

The compound of the formula (I) wherein R is SH and A is a group which forms a polyoxyethylene alkylphenyl ether can be produced by chlorinating hydroxyl group of the polyoxyethylene alkylphenyl ether with thionyl chloride [J. Am. Che. Soc., 60, 2540 (1938)], followed by reaction with sodium hydrosulfide [J. Am. Chem. Soc., 72, 1843 (1950)).

For immunization of an animal, the animal is inoculated with the complex thus obtained. Examples of animals to be inoculated include goat, sheep, rabbit, rat, mouse, guinea pig, chicken and the like. In case that a monoclonal antibody (hereinafter, sometimes, abbreviated to MoAb) against LAS or APE is desired, a mouse is particularly preferred.

The inoculation can be carried out according to a conventional method. For example, a mouse is inoculated with 1 to 100 μg, preferably 50 to 100 μg of the immunogen which is emulsified with equal amounts (0.1 ml) of physiological saline and Freund's complete adjuvant or RIBI adjuvant system per once at the back or abdomen subcutaneously or intraperitoneally. The mouse receives the inoculation 3 to 6 times at 2 to 3 week intervals.

Among the immunized animals, for example, mice, the individual having a high antibody titer is selected and, 3 to 5 days after the final immunization, the spleen or lymph node is collected. Then, the antibody producing cells contained therein are fused together with myeloma cells.

The fusion can be carried out by a known method and as a fusion promoting agent, for example, polyethylene glycol (hereinafter abbreviated to PEG) or Sendai virus (HVJ) can be used. PEG is preferred.

As myeloma cells, for example, NS-1, P3U1 or Sp2/O can be used and, in particular, P3U1 is preferred. For example, the preferred proportion of the spleen cells : myeloma cells is 1:1 to 10:1 and PEG having a molecular weight of 1,000 to 6,000 is added thereto in concentration of 10 to 80%. Desirably, the mixture is incubated at 20 to 37° C., preferably, at 30 to 37° C. for 3 to 10 minutes.

For screening of the desired hybridoma, various methods can be employed. For example, there is ELISA, wherein a supernatant of a hybridoma culture is added to a microplate on which OVA combined with SPC or NP7EC has been adsorbed and then an anti-mouse immunoglobulin antibody labeled with horseradish peroxidase (hereinafter abbreviated to HRP) is added thereto to detect the antibody combined to the solid phase of the plate. A hybridoma having positive antibody activity is subjected to cloning immediately. Normally, this can be readily carried out by limiting dilution analysis or the like.

The antibody titer of cloned hybridomas is determined by the above method and a hybridoma which constantly produces an antibody having high titer is selected to obtain the desired monoclonal hybridoma.

Examples of the antibody producing hybridoma obtained by the above described method include mouse hybridomas GOT930-9, GOT935-54 and MOF3-139 as described in Examples hereinafter.

The monoclonal antibodies against surfactant compounds for synthetic detergents or degradation products thereof which are produced by the hybridomas of the present invention are also included in the scope of the present invention.

The production of the monoclonal antibody by the hybridoma and the purification thereof can also be carried out by a per se known method. The monoclonal antibody thus obtained can serve as not only an antibody against the surfactant compound for synthetic detergents or their degradation products but also the compound of the formula (I).

The monoclonal antibody thus obtained can be prepared in the form of a solid phase antibody by a known method such as bromocyanate method described in "Taisha", Vol. 8, 696 (1971), glutaraldehyde (hereinafter abbreviated to GLA) and the like. Further, as preferred simpler and easier methods, there are a method wherein the antibody is physically adsorbed on, for example, a microplate, tube or polystyrene particles, a method utilizing immunochromatography, and the like.

They can be combined with enzymes for ELISA, buffers and the like to obtain a kit for immunoassay of detergents, their degradation products or a mixture thereof and such a kit is also included in the scope of the present invention.

In the immunoassay of the present invention, a so-called competitive assay is employed. That is, the quantitative determination can be carried out by quantitatively measuring competition between a specimen (e.g., water and soil samples containing detergents, their degradation products or a mixture thereof) and a known amount of labeled detergent, its degradation product or a mixture thereof for linking to the monoclonal antibody of the present invention. In such competitive assay, a given amount of an antibody supported on a carrier is added to a specimen solution containing an unknown antigen and further a given amount of an antigen labeled with a labeling agent. The amount of the labeling agent supported by the carrier or the amount of the labeling agent which does not supported by the carrier is measured. Desirably, the specimen and the labeled antigen are added almost at once.

In general, in comparison with sandwich method or the like, the competitive assay can be carried out by a simpler and easier operation within a shorter period of time.

Examples of the agent for labeling the antigen include radioisotopes (hereinafter abbreviated to RI), enzymes, enzyme substrates, fluorescent materials, biotin and the like. For linking the labeling agent to the antigen, maleimide method [J. Biochem., 79, 233 (1976)], active biotin method [J. Am. Chem. Soc., 100, 3585 (1978)] and the like can be used.

For example, in the case of LAS, a specific immunochemical determination by the competitive assay can be carried out by adding a solid phase, to which the antibody is linked physically or chemically by a know conventional means, to a sample to be tested, which contains an unknown amount of LAS, to allow to react. At the same time, a given amount of an antigen labeled with a labeling agent is added thereto to allow to react. Then, normally, the solid phase is washed thoroughly and the activity of the labeling agent linked to the solid phase is measured. When the labeling agent is RI, the measurement is carried out with a well counter or a liquid scintillation counter. When the labeling agent is an enzyme, its substrate is added, the mixture is allowed to stand and then the enzymatic activity is measured by colorimetry or fluorometry. When the labeling agent is a fluorescent material or a luminous material, it is measured according to a known method.

Since the monoclonal antibody having a high specificity is used, the immunoassay of the present invention has such a very advantageous characteristic that the specific determination of LAS, APE and their degradation products can be carried out without an error due to cross reaction with compounds other than LAS, APE and their degradation products, for example, compounds having a benzene ring such as toluene, phenol, benzene and aniline, or other surfactants.

Thus, in the present invention, by using the antibody having very high specificity for detergents and their degradation products, influence of other chemical substances in a specimen can be eliminated and therefore the determination can be simply and readily carried out with high sensitivity and specificity. Therefore, the present invention is useful for not only academic analyses but also investigation of influence of detergents and their degradation products on environmental preservation and the like.

The following Examples further illustrate the present invention in detail but are not to be construed to limit the scope thereof.

Although the following Examples are directed to LAS, SPC, SDS and APE, they are applicable to other surfactants for synthetic detergents in the same way. In addition, the mouse—mouse hybridomas GOT930-9 and GOT935-54 have been deposited at National Institute of Bioscience and Human-Technology (NIBH), Agency of Industrial Science & Technology, Ministry of International Trade & Industry since Sep.25, 1996 (date of the original deposit) under Budapest Treaty under the accession numbers of FERM BP-6065 and FERM BP-6066, respectively. The hybridoma MOF3-139 has been deposited since Aug.13, 1997 under Budapest Treaty under the accession umber of FERM BP-6059.

EXAMPLE 1

Production of anti-hapten monoclonal antibody (1) Preparation of immunogen

The haptens, SPC and NP7EC, were synthesized from phenyl valerate and nonylphenolethoxylate by a known method, respectively. An aqueous solution of the hapten (50 mg/ml) was added to an aqueous solution of BSA (50 mg/4 ml). To the mixture was slowly added dropwise 1 ral of an aqueous solution of water-soluble carbodiimide (50 rag/ml) with ice-cooling. The resultant mixture was reacted for 5 hours. After dialyzing with 3 liter of distilled water 5 times, the reaction mixture was lyophilized and stored so as to use as an immunogen.

(2) Immunization

To the complex of the hapten and BSA (500 μg/ml physiological saline) was added the equal amount of Freund's complete adjuvant and the mixture was thoroughly emulsified. Then, it was inoculated into BALB/c mice (female, 100 μg/0.4 ml/mouse) at their abdomens and backs subcutaneously and booster immunization was conducted 2 week intervals. After immunizing booster 6 times, the same complex solution (30 μg/0.1 ml physiological saline/mouse) was administered to individuals which showed maximum serum antibody titers in 2 weeks intravenously.

(3) Cell fusion

Three days after the last immunization, the spleen was excised from the abdomen of each mouse and a suspension of spleen cells (about $10^8$ cells) was prepared according to a conventional manner. Then, mouse myeloma cells (P3U1) ($2 \times 10^7$ cells) which had been washed with a serum-free culture medium three times were added thereto and subjected to cell fusion with PEG 6000 according to the method disclosed by Koehler and Milstein [Nature, 256, 495 (1975)].

After completion of the fusion, the cell mixture was suspended in so-called HAT medium containing hypoxanthine, aminopterin and thymidine and cultivated for 10 days. Cells originating from the spleen died out during the 10 days cultivation period spontaneously and P3U1 strain which did not fused together with the spleen cells also died out due to HAT medium. The cells which survived in the medium were regarded as hybridomas and then cultivation was continued by replacing the medium with HT medium corresponding to aminopterin-free HAT medium.

(4) Primary selection and cloning of hybridomas

An antibody titer of the supernatant of the hybridoma culture was measured by ELISA using a microplate in which a complex of the hapten and OVA (hereinafter abbreviated to hapten-OVA) was adsorbed on the solid phase. From 10 days to 20 days after fusion, the appearance of hybridomas were observed and the appearance of an antibody which linked to the hapten-OVA was recognized. Hybridomas which produced antibodies showing especially high binding activity were subjected to cloning by limiting dilution analysis.

(5) Secondary selection of hybridomas (5)-1 Selection of anti-LAS antibody, anti-SPC antibody and anti-SDS antibody-producing hybridomas A compound such as LAS, SPC, SDS, benzene sulfonate, toluene, benzene or phenol was added to the supernatant of the hybridoma culture obtained in the above (4) and the hybridoma was subjected to binding inhibitory examination wherein inhibition of linking to a SPC-OVA-adsorbing microplate was examined and a hybridoma whose linkage was inhibited by only LAS or LAS, SPC and SDS and was not influenced by other compounds was selected.

As a result, hybridoma GOT935-54 which produced a monoclonal antibody specifically linking to LAS and hybridoma GOT930-9 which produced a monoclonal antibody specifically linking to LAS, SPC and SDS were obtained. According to the determination of ELISA, the immunoglobulin class and subclass of these monoclonal antibodies were IgG1.

(5)-2 Selection of anti-APE antibody-producing hybridoma

A compound such as APE, APE degradation products (hereinafter, sometimes, abbreviated to APEC) or PEG was added to the supernatant of the culture of hybridoma obtained in the above (4) and the hybridoma was subjected to linking inhibitory examination wherein inhibition of linking to a microplate on which OVA combined with NP7EC had been adsorbed was examined and a hybridoma whose linkage was inhibited by only APE and APEC and was not influenced by other compounds was selected.

As a result, hybridoma MOF3-139 which produced a monoclonal antibody which specifically link to APE and APEC was obtained. According to the determination of ELISA, the immunoglobulin class and subclass of this monoclonal antibody was IgG1.

The materials determined, haptens used, hybridomas obtained and their accession Nos. are summarized in Table 1.

TABLE 1

| Material | Hapten | Hybridoma | Accession No. |
|----------|--------|-----------|---------------|
| LAS | SPC | GOT935-54 | FERM BP-6066 |
| SPC | SPC | GOT930-9 | FERM BP-6065 |
| SDS | SPC | GOT930-9 | FERM BP-6065 |
| APE | NP7EC | MOF3-139 | FERM BP-6059 |

(6) Production of monoclonal antibody

The cloned hybridoma was cultivated by incubating it in Daigo T medium (Nippon Seiyaku, Tokyo, Japan) containing 10% bovine fetal serum at 37° C. under 5% $CO_2$ and the antibody was obtained from the supernatant of the culture.

On the other hand, for obtaining a large amount of antibody, 0.5 ml of mineral oil was administered to a BALB/c mouse intraperitoneally and then $5 \times 10^6$ cells of hybridoma were inoculated in the mouse intraperitoneally. After about 10 days, the collection of ascites fluid was observed in the mouse that received inoculation of the cells and the ascites fluid was harvested from the peritoneal cavity by abdominal section of the mouse.

The purification of the antibody was carried out by fractionating a fraction from the supernatant of cell culture or ascites fluid with 45 to 50% saturated ammonium sulfate according to a conventional method and subjecting to column chromatography on a protein A column. 2 to 20 mg of the monoclonal antibody was obtained from 2 ml of the supernatant of ascites fluid depending upon the particular cell strain. When the purified monoclonal antibodies were subjected to electrophoresis on SDS polyacrylam:ide gel, they showed more than 96% purity.

EXAMPLE 2

Determination of LAS and LAS degradation products (1) Preparation of HRP labeled SPC HRP was dissolved in distilled water (4 mg/0.2 ml) and mixed with SPC (10 mg/0.2 ml) and to the mixture was added dropwise water-soluble carbodiimide solution (15 mg/0.1 ml) with stirring on ice. The mixture was allowed to react on ice for about 8 hours and then dialyzed sufficiently against PBS (−) to remove unreacted SPC and WSC.

(2) Preparation of solid phase monoclonal antibody

The antibody obtained in Example 1 (5)-1 was dissolved in 25 mM bis-Tris buffer at concentration of 5 μg/ml and distributed in each well of a 96-well immunoplate (manufactured by Nunc, Denmark). The plate was allowed to stand at 4° C. overnight to prepare the solid phase monoclonal antibody. For blocking the binding group, 150 μl aliquots of a Block Ace solution (manufactured by Snow Brand Milk Products, Tokyo) containing 0.01% sodium merthiolate (Sigma, U.S.A.) were distributed to the solid phase antibody. The antibody was stored at 4° C. until it was used.

(3) Determination of LAS and LAS degradation products

LAS, SPC and SDS diluted with distilled water were mixed with the equal amount of HRP labelled SPC prepared in the above (1) (2 µg/ml) (0.02% Tween 20—PBS) and the mixture was added to each well of the antibody-binding microplate prepared in the above (2). After reaction at room temperature for 90 minutes, the plate was washed with PBS and 100 µl of the enzyme substrate (TMBZ 0.1 mg/ml, 40 mM citrate buffer containing urea hydrogen peroxide 0.35 mg/ml, pH 5.0) was added. The color developing reaction was conducted for 15 minutes and the reaction was stopped with iN phosphoric acid. Then, absorbance at 450 nm was measured.

Figure 1:
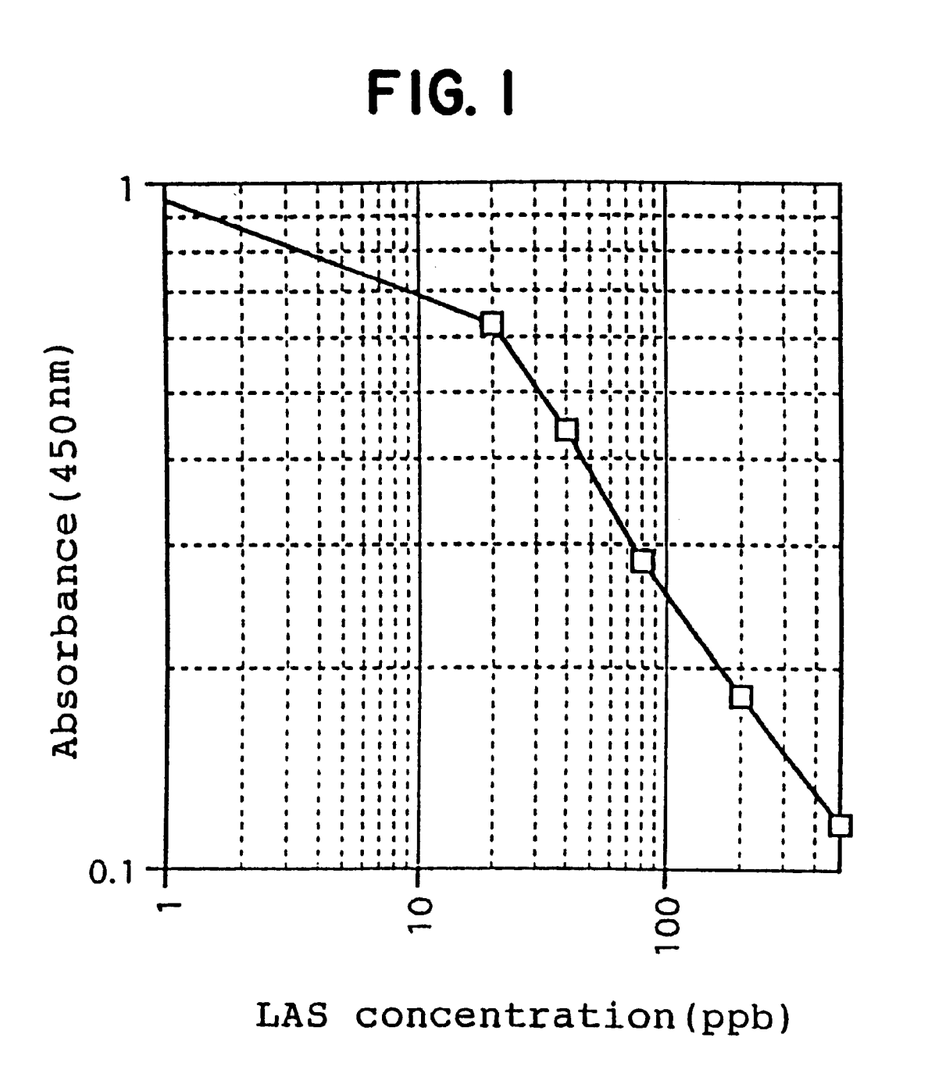
FIG. 1 is a calibration curve for determination of LAS.
Figure 2:
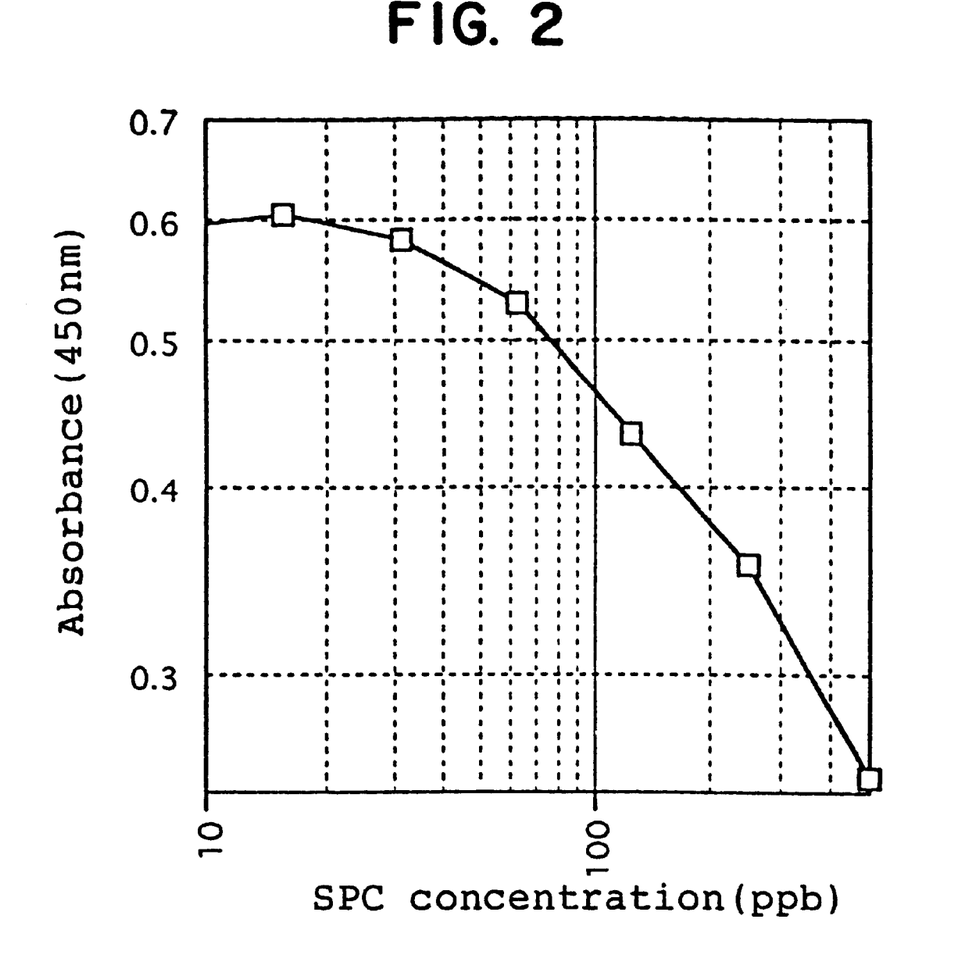
FIG. 2 is a calibration curve for determination of sulfophenyl valerate (hereinafter sometimes abbreviated to SPC).
Figure 3:
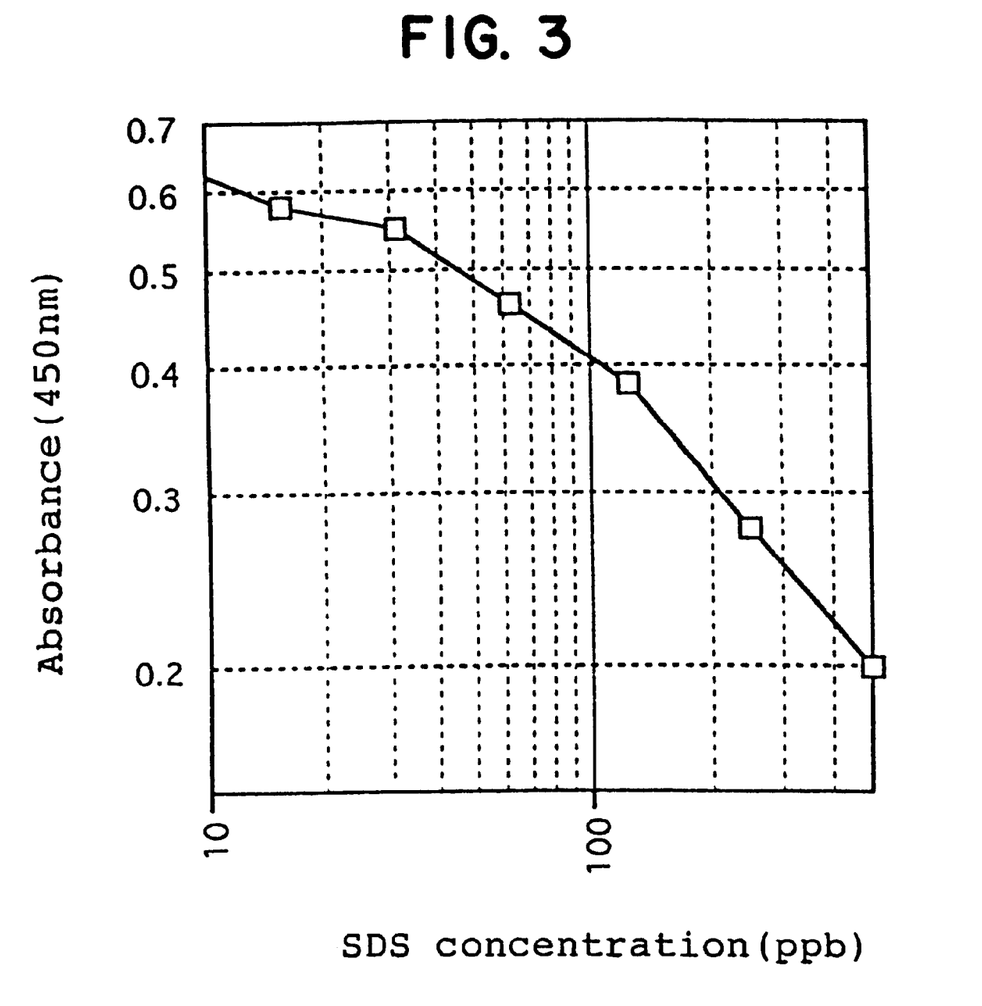
FIG. 3 is a calibration curve for determination of sodium dodecyl sulfate (SDS).

The calibration curves of LAS, SPC and SDS are shown in FIGS. 1, 2 and 3, respectively. In this system, about 20 to 500 ppb of LAS and about 50 to 500 ppb of SPC and SDS were able to be determined.

EXAMPLE 3

Determination of APE (1) Preparation of HRP labelled NP7EC

HRP was dissolved in 0.13 M aqueous $NaHCO_3$ solution (3.3 mg/2 ml) and mixed with NP7EC (300 µg/5 µl DMSO) which formed its activated ester by a known method. The mixture was allowed to react overnight at 4° C. and then dialyzed sufficiently against PBS (−) to remove unreacted NP7EC.

(2) Preparation of solid phase monoclonal antibody

The antibody obtained in Example 1 (5)-2 was dissolved in PBS (−) at concentration of 5 µg/ml and, according to the same manner as described in Example 2 (2), the solid phase thereof was formed on the 96-well immunoplate.

(3) Determination of APE and APE degradation products

APE (Tokyo Kasei) diluted with 60% aqueous methanol was mixed with the equal amount of HRP labeled NP7EC prepared in the above (1) (0.3 µg/ml) (0.1% Tween 20—double concentrated PBS) and the mixture was added to each well of the antibody-binding microplate prepared in the above (2). After reaction at room temperature for 90 minutes, the plate was washed with PBS containing 0.05% Tween 20 and 100 µl of the enzyme substrate (TMBZ 0.1 mg/ml, 40 mM citrate buffer containing urea hydrogen peroxide 0.35 mg/ml, pH 5.0) was added. The color developing reaction was conducted for 15 minutes and the reaction was stopped with 1N phosphoric acid. Then, absorbance at 450 nm was measured.

Figure 4:
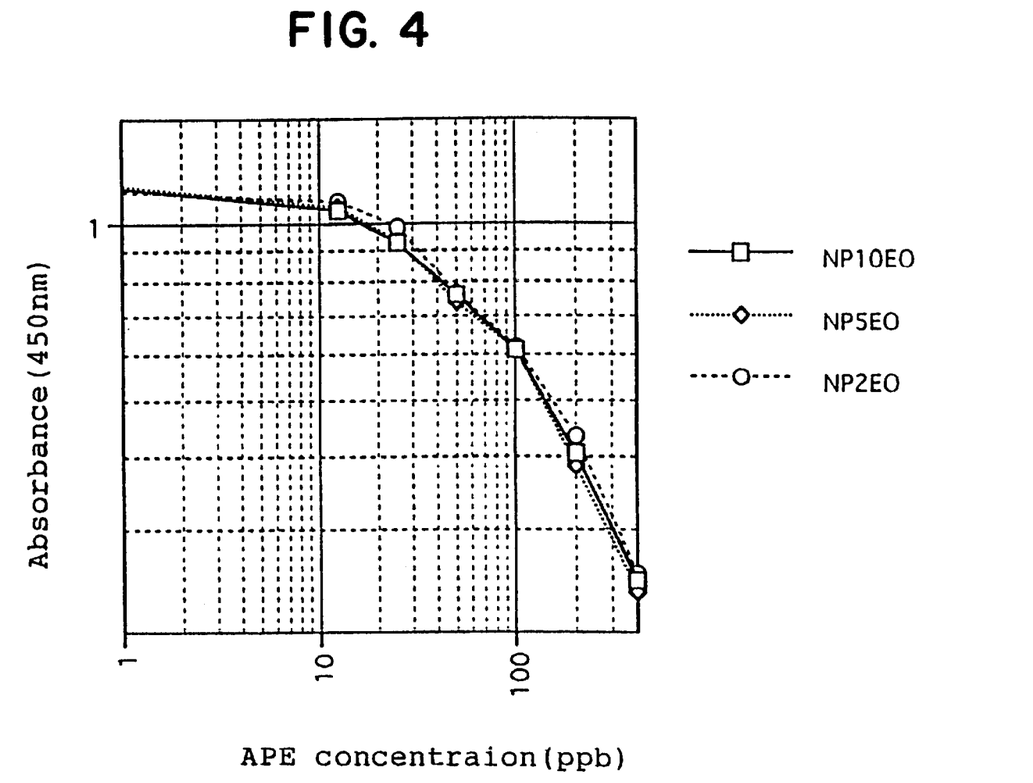
FIG. 4 is a calibration curve for determination of polyoxyethylene alkylphenyl ether (hereinafter sometimes abbreviated to APE).

The calibration curve of APE is shown in FIG. 4. In this system, about 50 to 500 ppb of APE was able to be determined.

As described hereinabove, according to the present invention, detergents and their degradation products can be simply and readily determined with high sensitivity and specificity, and such determination can be utilized not only in academic area but also in environmental preservation.

What is claimed is:

1. A hybridoma obtainable by fusing a spleen cell or lymphocyte of an animal immunized by a complex of a surfactant compound for synthetic detergent and protein together with a myeloma cell, which produces a monoclonal antibody against the compound or its degradation product.

2. A hybridoma according to claim 1, wherein the surfactant compound for synthetic detergent is an anionic surfactant compound.

3. A hybridoma according to claim 2, wherein the anionic surfactant compound is a compound selected from the group consisting of alkylsulfuric acid, alkylbenzenesulfonic acid, alkylnaphthalenesulfonic acid, naphthalenesulfonic acid formaldehyde condensate and their salts.

4. A hybridoma according to claim 2, wherein the anionic surfactant compound is a linear alkylbenzenesulfonic acid or a salt thereof.

5. A hybridoma according to claim 1, wherein the surfactant compound for synthetic detergent is a nonionic surfactant compound.

6. A hybridoma according to claim 5, wherein the nonionic surfactant compound is a compound selected from the group consisting of polyoxyehtylene alkylphenyl ether, polyoxyethylene alkyl ether, polyoxyether polystyrylphenyl ether, polyoxyethylene styrenated phenyl ether and their salts.

7. A hybridoma according to claim 1, which is mouse-mouse hybridoma GOT930-9, GOT935-54, or MOF3-139.

8. A monoclonal antibody against a surfactant compound for synthetic detergent or its degradation product which is produced by the hybridoma obtainable by fusing a spleen cell or lymphocyte of an animal immunized by a complex of the surfactant compound for synthetic detergent and protein together with a myeloma cell.

9. A monoclonal antibody according to claim 8, wherein the surfactant compound for synthetic detergent is an anionic surfactant compound.

10. A monoclonal antibody according to claim 9, wherein the anionic surfactant compound is a compound selected from the group consisting of alkylsulfuric acid, alkylbenzenesulfonic acid, alkylnaphthalenesulfonic acid, naphthalenesulfonic acid formaldehyde condensate and their salts.

11. A monoclonal antibody according to claim 9, wherein the anionic surfactant compound is a linear alkylbenzenesulfonic acid or a salt thereof.

12. A kit for immunoassay of a detergent, its degradation product or a mixture thereof comprising as an essential constitutional component the monoclonal antibody according to claim 10.

13. A method for immunoassay of a detergent, its degradation product or a mixture thereof in a specimen which comprises reacting the specimen with the monoclonal antibody of according to claim 10 supported on a carrier and the detergent, its degradation product or the mixture thereof labeled with a labeling agent.

14. A kit for immunoassay of a detergent, its degradation product or a mixture thereof comprising as an essential constitutional component the monoclonal antibody according to claim 11.

15. A method for immunoassay of a detergent, its degradation product or a mixture thereof in a specimen which comprises reacting the specimen with the monoclonal antibody of according to claim 11 supported on a carrier and the detergent, its degradation product or the mixture thereof labeled with a labeling agent.

16. A kit for immunoassay of a detergent, its degradation product or a mixture thereof comprising as an essential constitutional component the monoclonal antibody according to claim 9.

17. A method for immunoassay of a detergent, its degradation product or a mixture thereof in a specimen which comprises reacting the specimen with the monoclonal antibody of according to claim 9 supported on a carrier and the detergent, its degradation product or the mixture thereof labeled with a labeling agent.

18. A monoclonal antibody according to claim 8, wherein the surfactant compound for synthetic detergent is a nonionic surfactant compound.

19. A kit for immunoassay of a detergent, its degradation product or a mixture thereof comprising as an essential constitutional component the monoclonal antibody according to claim 18.

20. A monoclonal antibody according to claim 18, wherein the nonionic surfactant compound is a compound selected from the group consisting of polyoxyehtylene alkylphenyl ether, polyoxyethylene alkyl ether, polyoxyether polystyrylphenyl ether, polyoxyethylene styrenated phenyl ether and their salts.

21. A kit for immunoassay of a detergent, its degradation product or a mixture thereof comprising as an essential constitutional component the monoclonal antibody according to claim 20.

22. A method for immunoassay of a detergent, its degradation product or a mixture thereof in a specimen which comprises reacting the specimen with the monoclonal antibody of according to claim 20 supported on a carrier and the detergent, its degradation product or the mixture thereof labeled with a labeling agent.

23. A method for immunoassay of a detergent, its degradation product or a mixture thereof in a specimen which comprises reacting the specimen with the monoclonal antibody of according to claim 18 supported on a carrier and the detergent, its degradation product or the mixture thereof labeled with a labeling agent.

24. A method for immunoassay of detergent, its degradation product or a mixture thereof in a specimen which comprises reacting the specimen with the monoclonal antibody of according to claim 8 supported on a carrier and the detergent, its degradation product or the mixture thereof labeled with a labeling agent.

25. A monoclonal antibody according to claim 8, which is produced by mouse-mouse hybridoma GOT930-9, GOT935-54, or MOF3-139.

26. A kit for immunoassay of a detergent, its degradation product or a mixture thereof comprising as an essential constitutional component the monoclonal antibody according to claim 8.

27. A method for immunoassay of a detergent in a specimen, which comprises reacting the specimen with the monoclonal antibody produced by the hybridoma GOT930-9, wherein the detergent is selected from the group consisting of sulfophenol valerate, sodium dodecyl sulfate, and the sodium salt of butyl naphthalene sulfate.

28. A method for immunoassay of a detergent in a specimen, which comprises reacting the specimen with the monoclonal antibody produced by the hybridoma GOT935-54, wherein the detergent is a linear alkyl benzenesulfonate.

29. A method for immunoassay of a detergent in a specimen, which comprises reacting the specimen with the monoclonal antibody produced by the hybridoma MOF3-139, wherein the detergent is a polyoxyethylene alkylphenyl ether.

30. A kit for immunoassay of a detergent, its degradation product or a mixture thereof comprising as an essential constitutional component the monoclonal antibody according to claim 25.

31. A method for immunoassay of a detergent, its degradation product or a mixture thereof in a specimen which comprises reacting the specimen with the monoclonal antibody according to claim 25 supported on a carrier and the detergent, its degradation product or the mixture thereof labeled with a labeling agent.

* * * * *